(12) United States Patent
Hara et al.

(10) Patent No.: US 9,940,737 B2
(45) Date of Patent: Apr. 10, 2018

(54) ANALYZER, ANALYSIS METHOD AND ANALYSIS PROGRAM OF BONE MINERAL DENSITY

(71) Applicant: Rigaku Corporation, Tokyo (JP)

(72) Inventors: Yukihiro Hara, Hino (JP); Takafumi Koike, Tokyo (JP); Minoru Maesawa, Musashimurayama (JP)

(73) Assignee: RIGAKU CORPORATION, Tokyo (JP)

( * ) Notice: Subject to any disclaimer, the term of this patent is extended or adjusted under 35 U.S.C. 154(b) by 10 days.

(21) Appl. No.: 15/285,708

(22) Filed: Oct. 5, 2016

(65) Prior Publication Data
US 2017/0098315 A1 Apr. 6, 2017

(30) Foreign Application Priority Data
Oct. 6, 2015 (JP) .................... 2015-198890

(51) Int. Cl.
*G06K 9/00* (2006.01)
*G06T 11/00* (2006.01)
(Continued)

(52) U.S. Cl.
CPC ............ *G06T 11/005* (2013.01); *A61B 6/032* (2013.01); *A61B 6/505* (2013.01); *A61B 6/5211* (2013.01);
(Continued)

(58) Field of Classification Search
USPC ........ 382/100, 103, 106, 128–134, 154–155, 382/162, 168, 172–173, 181, 193, 199, 382/220, 224, 232, 254, 274, 276, 286, 382/291, 294, 305, 312; 378/4, 21, 196, 378/162, 146; 600/407, 410
See application file for complete search history.

(56) References Cited

U.S. PATENT DOCUMENTS 5,034,969 A * 7/1991 Ozaki ................... A61B 6/583
378/162
2001/0053202 A1* 12/2001 Mazess ............... A61B 6/4225
378/196

(Continued)

FOREIGN PATENT DOCUMENTS

JP 2778707 B2 7/1998
JP 11-155852 A 6/1999

*Primary Examiner* — Seyed Azarian
(74) *Attorney, Agent, or Firm* — Birch, Stewart, Kolasch & Birch, LLP (57) ABSTRACT

To make a user easily obtain an objective and stable analysis result of bone mineral density. An analyzer 100 of bone mineral density using CT image data of a phantom having a known bone mineral density includes: a known data storage part 105 that stores known data of bone mineral density for a phantom; a histogram production part 102 that produces a histogram of region number relative to a CT value for three-dimensional CT image data of the phantom; a correspondence determination part 106 that determines correspondence between a CT value and a bone mineral density by correlating CT values showing respective peaks of the produced histogram with the known data of the phantom; and an analysis part 109 that decides a bone mineral density for three-dimensional CT image data of a subject using the determined correspondence.

6 Claims, 12 Drawing Sheets

(51) Int. Cl.
*A61B 6/03* (2006.01)
*G06T 1/60* (2006.01)
*G06T 7/00* (2017.01)
G21K 5/10 (2006.01)
A61B 6/00 (2006.01)

(52) U.S. Cl.
CPC ............... *A61B 6/583* (2013.01); *G06T 1/60* (2013.01); *G06T 7/0012* (2013.01); A61B 6/4435 (2013.01); G06T 2207/10072 (2013.01); G06T 2207/20072 (2013.01); G06T 2207/30008 (2013.01)

(56) References Cited

U.S. PATENT DOCUMENTS

| | | | |
|---|---|---|---|
| 2007/0055136 A1* | 3/2007 | Yamamoto | A61B 5/417 600/410 |
| 2011/0040168 A1* | 2/2011 | Arnaud | G06T 7/0012 600/407 |
| 2014/0126800 A1* | 5/2014 | Lang | A61B 6/505 382/132 |
| 2014/0355852 A1* | 12/2014 | Liew | A61B 6/482 382/128 |

* cited by examiner

| | | |
|---|---|---|
| WHOLE BONE | : BMD[mg/mm$^3$] | 287.1205 |
| WHOLE BONE | : TV[mm$^3$] | 4.26374 |
| WHOLE BONE | : BV[mm$^3$] | 2.27849 |
| WHOLE BONE | : BS[mm$^2$] | 28.98333 |
| WHOLE BONE | : BS/BV[1/mm] | 12.72041 |
| WHOLE BONE | : BV/TV[%] | 53.4 |
| CORTICAL BONE | : BMD[mg/mm$^3$] | 637.6162 |
| CORTICAL BONE | : TV[mm$^3$] | 0.90665 |
| CORTICAL BONE | : BV[mm$^3$] | 0.90665 |
| CORTICAL BONE | : BS[mm$^2$] | 8.99297 |
| CORTICAL BONE | : BS/BV[1/mm] | 9.91894 |
| CORTICAL BONE | : BV/TV[%] | 100 |
| CANCELLOUS BONE | : BMD[mg/mm$^3$] | 55.47946 |
| CANCELLOUS BONE | : TV[mm$^3$] | 3.3571 |
| CANCELLOUS BONE | : BV[mm$^3$] | 1.37184 |
| CANCELLOUS BONE | : BS[mm$^2$] | 19.99036 |
| CANCELLOUS BONE | : BS/BV[1/mm] | 14.57189 |
| CANCELLOUS BONE | : BV/TV[%] | 40.9 |

FIG. 9

ANALYZER, ANALYSIS METHOD AND ANALYSIS PROGRAM OF BONE MINERAL DENSITY

FIELD OF THE INVENTION

The present invention relates to an analyzer, an analysis method and an analysis program of a bone mineral density using CT image data of a phantom having a known bone mineral density.

DESCRIPTION OF THE RELATED ART

There is bone analysis as one of applications generally desired for X-ray CT image data. In the bone analysis, bone mineral density of bone of a subject can be measured by X-ray CT image data obtained by capturing the subject. Then, in order to carry out the bone analysis, it is necessary to prepare previously a calibration curve for converting a CT value being pixel information of three-dimensional CT image data into bone mineral density.

Until now, there has been known a method of obtaining a calibration curve using images obtained by CT scanning some phantoms of hydroxyapatite having different densities. With such a method, a user sets regions of interest so as to include each region of hydroxyapatite for images obtained by the capturing, and, from the relationship between a CT value in the region of interest and a bone mineral density of the phantom, the calibration curve that correlates the CT value with the bone mineral density can be calculated.

For example, the apparatus described in Patent Literature 1 produces a calibration curve between a CT value at the central portion of a CT image for calibration and hydroxyapatite concentration at the central portion based on projection data for calibration collected for a prescribed number of phantoms.

Further, the apparatus described in Patent Literature 2 recognizes an arrangement line having a prescribed relationship caused by a plurality of reference materials based on a physical property value of a reference material in image information of a captured phantom, recognizes a position of the reference material on the arrangement line recognized by a unit configured to recognize an arrangement based on a known physical property value, and sets a region of interest of a prescribed shape on the position recognized by a unit configured to confirm a reference material position.

Patent Literature

Patent Literature 1: Japanese Patent Laid-Open Publication No. H11-155852
Patent Literature 2: Japanese Patent No. 2778707

In the process of producing a calibration curve as described above, a region of interest is set by an input operation of a user. Accordingly, it is likely to occur that an appropriate region of interest is not set caused by an error of the operation, or that a region of interest different from a region to be set originally is set caused by misunderstanding, and objective and stable analysis can not be carried out. Further, the setting operation of a region of interest itself is not easy, and a user suffers too much work burden upon the setting.

SUMMARY OF THE INVENTION

The present invention has been achieved in view of such a situation, and aims to provide an analyzer, an analysis method and an analysis program of bone mineral density with which a user can easily obtain an objective and stable analysis result of bone mineral density.

(1) In order to achieve the above-described purpose, the analyzer of the present invention is an analyzer of bone mineral density using CT image data of a phantom whose bone mineral density is known, the analyzer including: a known data storage part that stores known data of bone mineral density for a phantom; a histogram production part that produces a histogram of region number relative to a CT value for three-dimensional CT image data of the phantom; a correspondence determination part that determines correspondence between a CT value and a bone mineral density by correlating CT values showing respective peaks of the produced histogram with the known data of the phantom; and an analysis part that decides a bone mineral density for three-dimensional CT image data of a subject using the determined correspondence.

As described above, the correspondence between a CT value and a bone mineral density is determined automatically using known data of bone mineral density of a phantom and CT image data, and, therefore, a user can easily obtain an objective and stable analysis result of bone mineral density.

(2) Further, in the analyzer of the present invention, the correspondence determination part discriminates that, when a peak is included in a range of a prescribed number of counts of the produced histogram, the peak is one to be correlated with the known data. This makes it possible to discriminate a peak that is significant on designing a phantom when establishing correspondence with a known bone mineral density, and to automatically determine the correspondence between a CT value and bone mineral density.

(3) Further, the analyzer of the present invention furthermore includes a display part that displays on a screen a region of three-dimensional CT image data of the phantom showing a peak to be correlated with the known data. This makes it possible to display a referred region on CT image data for a user, and enables the user to confirm that correct processing is being carried out.

(4) Further, in the analyzer of the present invention, the correspondence determination part determines a calibration curve between a CT value and a bone mineral density as the determined correspondence. This makes it possible to automatically produce a calibration curve of a CT value—bone mineral density without a difficult operation by a user.

(5) Further, in the analyzer of the present invention, the histogram production part produces a histogram of region number relative to a CT value using data of regions limited along a direction in which density of the phantom is uniform, in the three-dimensional CT image data. When an intended separative histogram using the whole image region is not obtained, it is possible to improve the separability of peaks in a histogram by limiting an image region to be used as described above.

(6) Moreover, an analysis method of the present invention is an analysis method of bone mineral density using CT image data of a phantom having a known bone mineral density, the method includes the steps of: producing a histogram of region number relative to a CT value for three-dimensional CT image data of the phantom; determining correspondence between a CT value and a bone mineral density by correlating CT values showing respective peaks of the produced histogram with known data of bone mineral density stored with respect to the phantom; and deciding a bone mineral density for three-dimensional CT image data of a subject using the determined correspondence. This makes it possible for a user to easily obtain an objective and stable analysis result of bone mineral density.

(7) In addition, an analysis program of the present invention is an analysis program of bone mineral density that is to be executed by a computer using CT image data of a phantom having a known bone mineral density, the program including the processes of: producing a histogram of region number relative to a CT value for three-dimensional CT image data of the phantom; determining correspondence between a CT value and a bone mineral density by correlating CT values showing respective peaks of the produced histogram with known data of bone mineral density stored with respect to the phantom; and deciding a bone mineral density for three-dimensional CT image data of a subject using the determined correspondence. This makes it possible for a user to easily obtain an objective and stable analysis result of bone mineral density.

According to the present invention, a user can easily obtain an objective and stable analysis result of bone mineral density.

DETAILED DESCRIPTION OF THE INVENTION

Next, embodiments of the present invention will be explained with reference to the drawings. In order to facilitate understanding of explanation, the same reference number is given to the same constituent element in respective drawings, and repeated explanation is omitted.

[Configuration of Measurement System]

Figure 1:
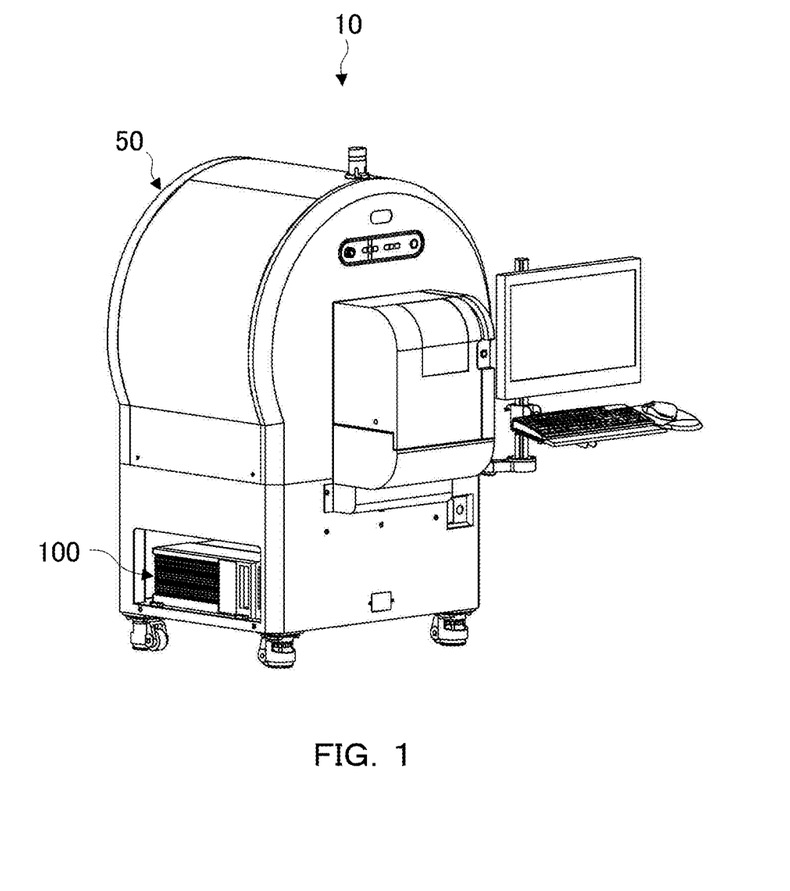
FIG. 1 is a schematic view showing a measurement system of the present invention.

FIG. 1 is a schematic view showing a measurement system 10 of bone mineral density. The measurement system 10 includes an X-ray CT apparatus 50 and an analyzer 100. The X-ray CT apparatus 50 has a microfocus X-ray source with an X-ray focus size of micrometer in unit and a two-dimensional X-ray detector, and converts X-rays received two-dimensionally into electric signals to create an image.

In the detection, a pixel size of tomographic image data may be set, for example, from 4.5 µm to 144 µm.

The X-ray source and detector are set up on a rotating arm, and rotate in 360 degrees around a prescribed rotation shaft. The X-ray CT apparatus 50 has a support for placing a subject such as rat or mouse, and the support is put into the inside of the X-ray CT apparatus 50 through a gantry hole by being slid. With the X-ray CT apparatus 50, three-dimensional CT image data of a phantom and a subject is captured, which is sent to the analyzer 100. The analyzer 100 measures bone mineral density using received CT image data.

[Configuration of Analyzer]

Figure 2:
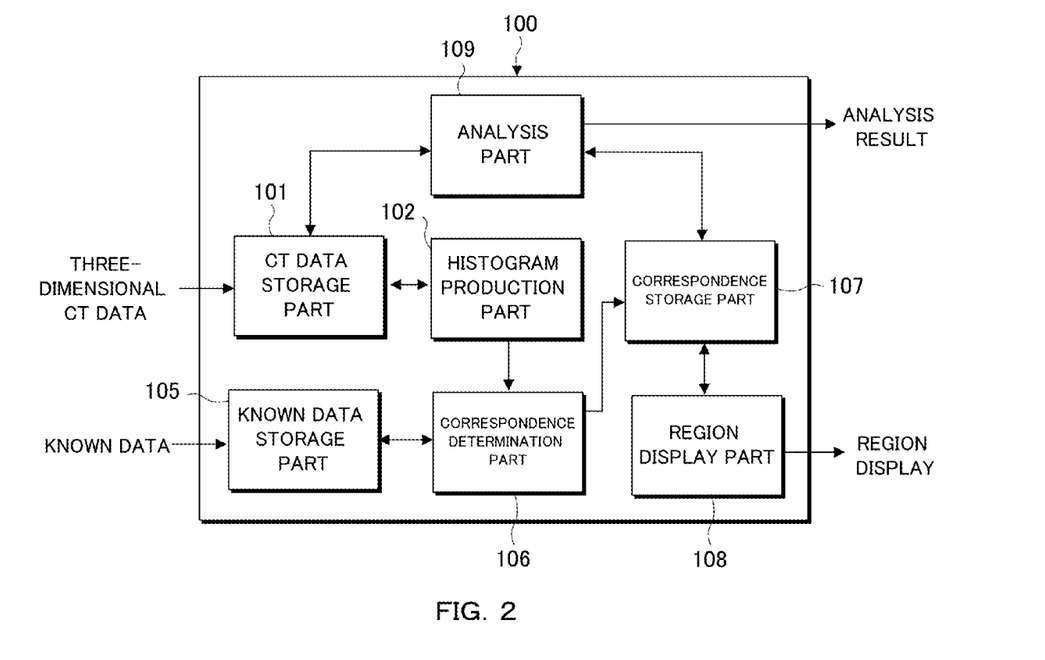
FIG. 2 is a block diagram showing a functional configuration of an analyzer of the present invention.

FIG. 2 is a block diagram showing a functional configuration of the analyzer 100. The analyzer 100 is configured, for example, from a PC having a memory, CPU etc., and measures bone mineral density (BMD value) of a subject. In measurement, correspondence between a CT value and a bone mineral density is determined using CT image data of a phantom having a known bone mineral density (for example, hydroxyapatite density), and, from the CT value, a bone mineral density is decided. As shown in FIG. 2, the analyzer 100 includes a CT image data storage part 101, a histogram production part 102, a known data storage part 105, a correspondence determination part 106, a correspondence storage part 107, a region display part 108 and an analysis part 109.

The CT image data storage part 101 stores three-dimensional CT image data of a phantom and a subject that has been captured with the X-ray CT apparatus 50 and sent. The three-dimensional CT image data may be data obtained from the others. The histogram production part 102 produces a histogram that sets region number (number of pixels) as a count number relative to a CT value, for the three-dimensional CT image data of the phantom.

The known data storage part 105 stores known data of bone mineral density with respect to a phantom. The known data of bone mineral density with respect to a phantom are, for example, known data that specify, relative to a specific bone mineral density part in the phantom, a uniform bone mineral density in the part. A specific configuration example of a phantom will be described later.

The correspondence determination part 106 correlates CT values showing respective peaks in the produced histogram with known data of a phantom, and determines correspondence between the CT value and bone mineral density. Specifically, it determines a calibration curve between the CT value and bone mineral density. This makes it possible to automatically produce a calibration curve of a CT value—bone mineral density without a difficult operation by a user.

In specifying a peak, preferably, when a peak is included in a range of a prescribed number of counts, the peak is specified as a peak to be correlated with known data. This makes it possible to discriminate a peak that is significant on designing a phantom when correlating a peak with known bone mineral density, and to automatically correlate a CT value with a bone mineral density. Meanwhile, in an instance where the range of a count number can be replaced by a range of CT values, the peak may be detected based on whether a peak is included in a prescribed range of CT values.

The correspondence storage part 107 stores the correspondence between the CT value and bone mineral density determined in the correspondence determination part 106. The region display part 108 controls a display screen, and displays the region of three-dimensional CT image data of a phantom showing a peak to be correlated with known data on the display screen. This makes it possible to display the region on CT image data referred to for a user, and enables the user to confirm that correct processing is being carried out.

The analysis part 109 decides a bone mineral density for three-dimensional CT image data of a subject using determined correspondence. Further, it controls so that the decision result is displayed on the display screen. In this way, the correspondence between a CT value and a bone mineral density is determined automatically using known data of bone mineral density of a phantom and CT image data, and, therefore, a user can easily obtain an objective and stable analysis result of bone mineral density.

[Operation of Analyzer]

Figure 3:
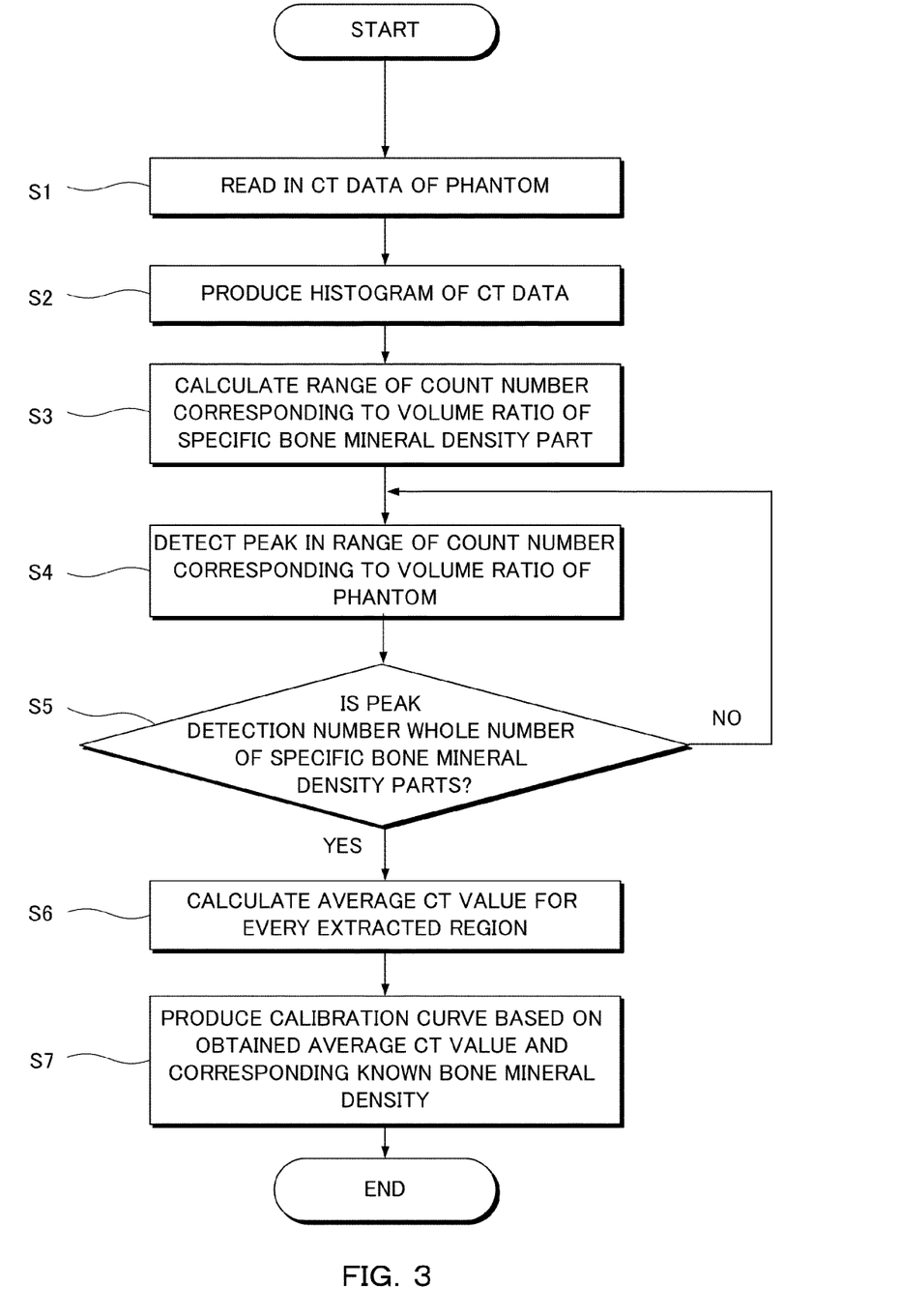
FIG. 3 is a flowchart showing the operation of the analyzer of the present invention.

FIG. 3 is a flowchart showing operations of the analyzer 100. In the analyzer 100, CT image data of a captured phantom are stored, and known data of bone mineral density with respect to the phantom are stored.

The analyzer 100 reads in CT image data of the captured phantom (Step S1). Then, using read in CT image data, it produces a histogram of a pixel number relative to a CT value (Step S2). CT image data to be the target on this occasion may be limited to those in some region (for example, the central region) of the phantom instead of those in the whole phantom. In the case of CT image data of a phantom, for a part with uniform bone mineral density, approximately the same CT values are obtained, and, therefore, in a produced histogram, peaks are formed only in a number of such specific bone mineral density parts.

Next, with respect to the phantom, a range of a prescribed number of counts corresponding to a volume ratio of the specific bone mineral density part is calculated (Step S3). Then, peaks are detected in the range of a prescribed number of counts corresponding to a volume ratio of the phantom (Step S4). Details of a specific detection method of a peak will be described later.

Whether or not the number of peak detection is the total number of specific bone mineral density parts is decided (Step S5). As the result of decision, when the number of peak detection is less than the total number of specific bone mineral density parts, the operation returns to Step S4, and detection of peaks is further continued. On the other hand, when the number of peak detection is equal to the total number of specific bone mineral density parts, an average CT value for every range extracted as a specific bone mineral density part is calculated as a CT value representing a peak for every peak (Step S6).

Next, using the obtained average CT value and corresponding known bone mineral density, a calibration curve is produced (Step S7). Details of the production of calibration curve will be described later. For CT image data of a captured subject, a bone mineral density relative to a CT value is specified using the produced calibration curve, and a bone mineral density of the subject is measured (Step S8). Meanwhile, the CT image data of a subject are sent after the capturing and are stored in the analyzer 100 that received the data. Furthermore, each process in the above-described analyzer 100 is carried out by executing a program.

EXAMPLES

Next, specific Examples will be explained. The Example is an instance, and is not one that limits the invention.

(Configuration of Phantom)

Figure 4A:
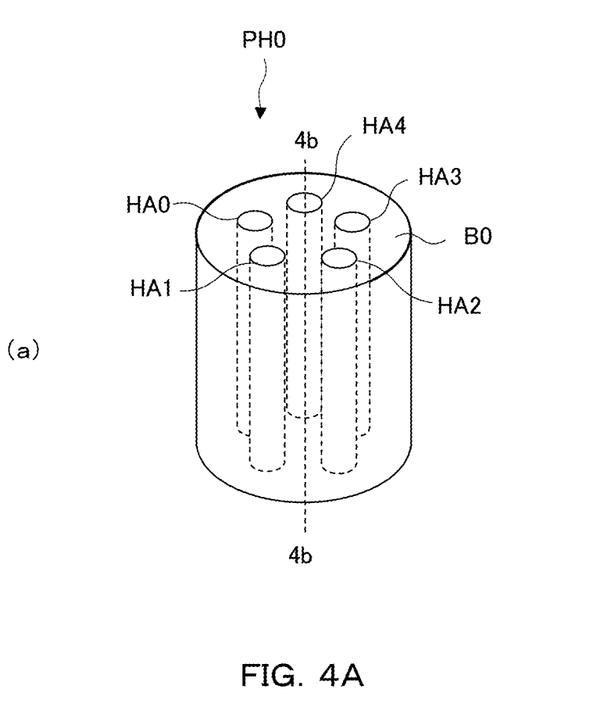
FIG. 4A is a perspective view showing a configuration of a phantom.
Figure 4B:
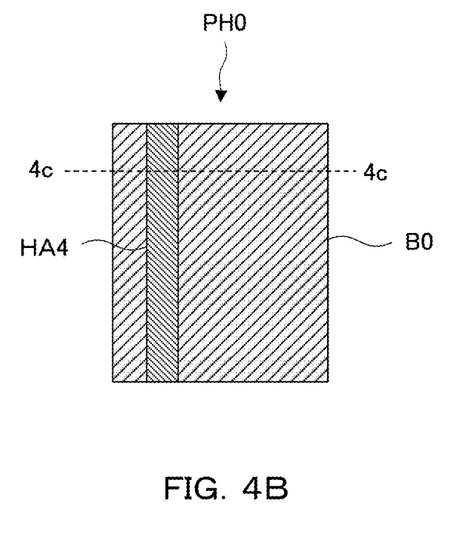
FIG. 4B is a side cross-sectional view showing a configuration of the phantom.
Figure 4C:
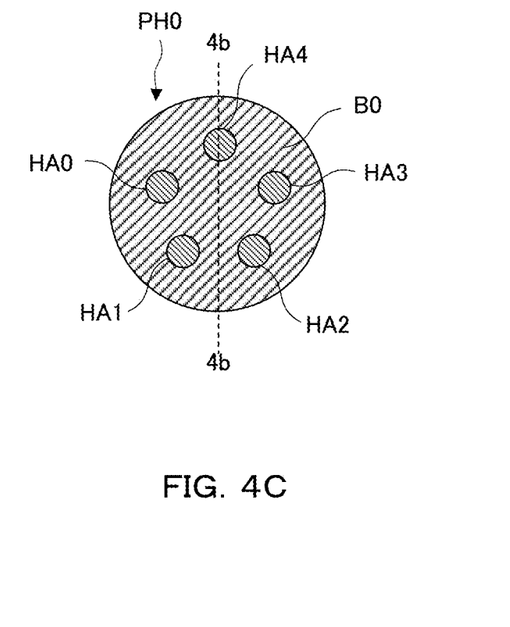
FIG. 4C is a plan cross-sectional view showing a configuration of the phantom.

FIGS. 4A to 4C are, respectively, a perspective view, a side cross-sectional view and a plan cross-sectional view, showing the configuration of a phantom PH0. The phantom PH0 shown in FIGS. 4A to 4C is an instance as a phantom. Instead of the phantom described above, another phantom that is a phantom having a detectable part with constant bone mineral density is also acceptable, and the shape etc. thereof are also not limited. Meanwhile, the cross-sections 4b and 4c in the drawings correspond to the cross-sections shown in FIGS. 4B and 4C.

The phantom PH0 has a columnar shape, and a main body B0 is configured from a resin material such as epoxy resin. Further, the phantom PH0 includes a plurality of bone mineral density parts HA0 to HA4 of a columnar shape formed by incorporating hydroxyapatite with constant density in resin, in the inside of the main body B0. In the bone mineral density parts HA0 to HA4, for example, powdery hydroxyapatite is dispersed, and the density thereof is adjusted with resin. As to densities of hydroxyapatite in respective parts, 50 mg/mm$^3$ in the bone mineral density part HA1, 200 mg/mm$^3$ in the bone mineral density part HA2, 800 mg/mm$^3$ in the bone mineral density part HA3, and 1200 mg/mm$^3$ in the bone mineral density part HA4. Meanwhile, the bone mineral density part HA0 does not contain hydroxyapatite, and is provided as a dummy.

(Specification of Peak)

When three-dimensional CT image data of the phantom PH0 is obtained using the X-ray CT apparatus 50, a histogram in which a region number (pixel number) is set as a count number relative to a CT value is produced using the CT image data. In the histogram, spread of a peak corresponding to a volume ratio with respect to respective bone mineral density parts in the phantom PH0 is generated. The spread of a peak is the range of the histogram.

For example, when a specific bone mineral density part exists in a columnar shape of 5 mm in diameter and 38 mm in length in the phantom PH0 and one pixel size of a CT image is 120 μm$^3$, the volume of the column is 2.5×2.5×π× 38=746.1 mm$^3$. Division of the volume by one pixel size gives 746.1 mm$^3$/0.12 mm$^3$=6218 (pieces), and the range of the histogram (number of pieces) is obtained.

Using the range of the above-described histogram (number of pieces), the histogram is counted from a higher value in the histogram. The range is determined while setting a point of the histogram having a certain number of counts or more (for example, five counts or more) as a starting point, and a point for which a certain number of pixels have been counted is set as an end point.

Figure 6:
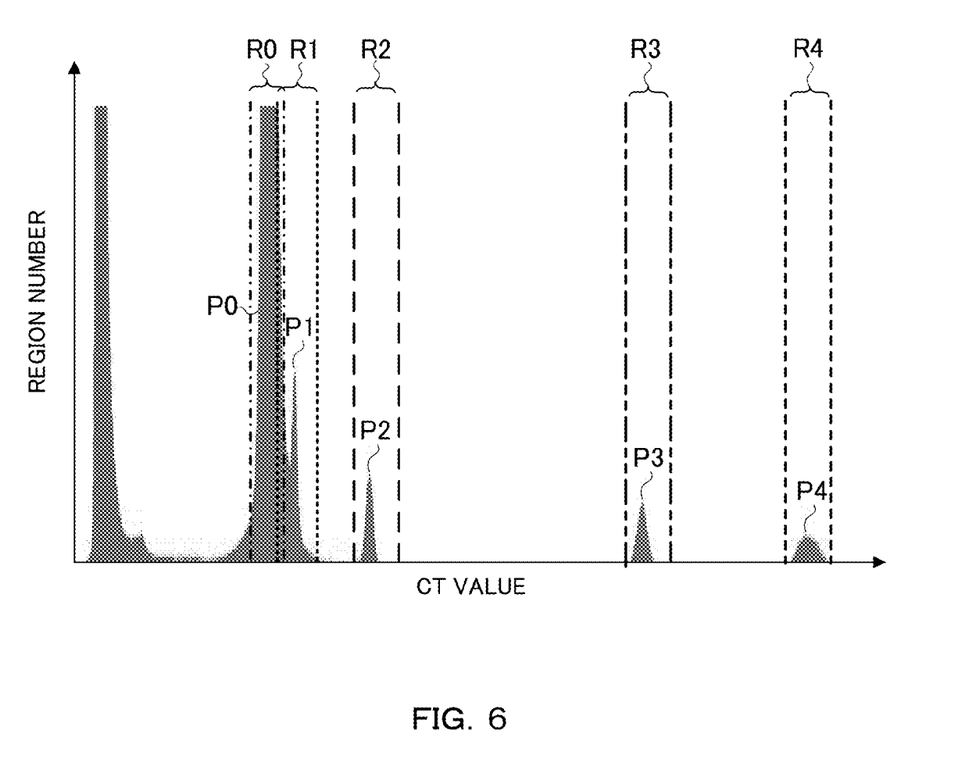
FIG. 6 is a drawing showing a histogram and width of a CT value.

For example, with respect to the peak P4 in FIG. 6, the count of number of pieces of the histogram in this peak range gives a value of near 6200. The peak P3 has a higher peak top than that of the peak P4, but has a narrower width correspondingly. However, the number of pieces of the histogram is near 6200, too. For the peaks P4, P3, and P2, a range including approximately a peak can be obtained by the above-described technique, and, therefore, the peak can be detected by obtaining the maximum value in the range.

Peaks P1 and P0 are adjacent to each other and can not be discriminated by the above-described technique. Accordingly, separation of peaks is carried out while referring to Changming Zhou, Takagi Mikio, "An Optimal Histogram Segmentation Method Using Peak Detection and Its Application to Threshold Selection," J. of Television Society, Vol. 45, No. 10, pp. 1179-1189, 1991), "3.2 Peak Examination Standard," and each of peaks is detected. The technique is effective when being applied to pieces where difference in previously set bone mineral contents is small (specifically, in an instance where it is 100 or less).

Figure 5A:
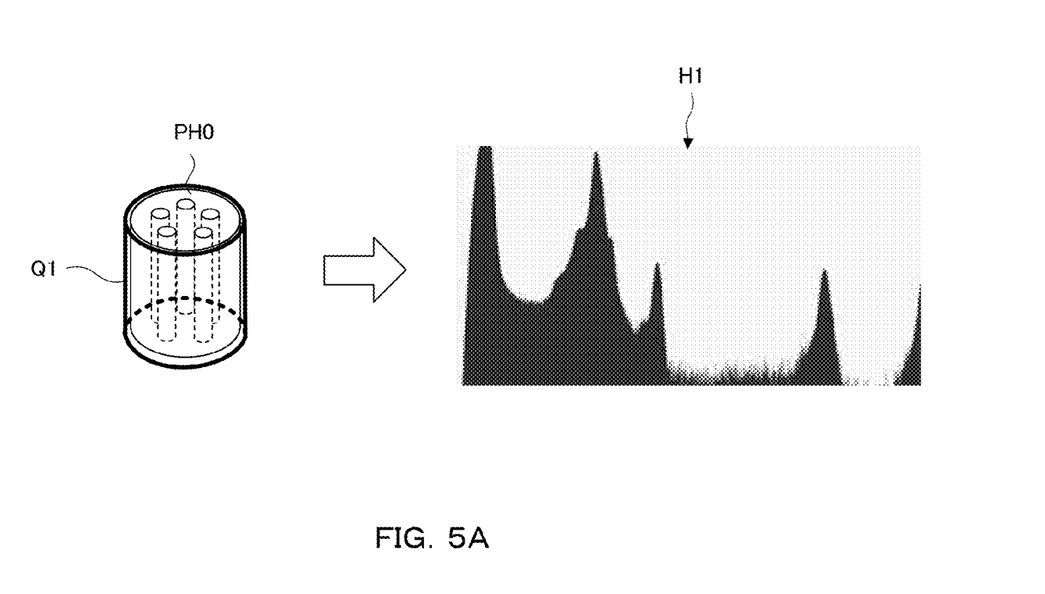
FIG. 5A is a drawing showing an image region for which a histogram is to be obtained and an example of the histogram.
Figure 5B:
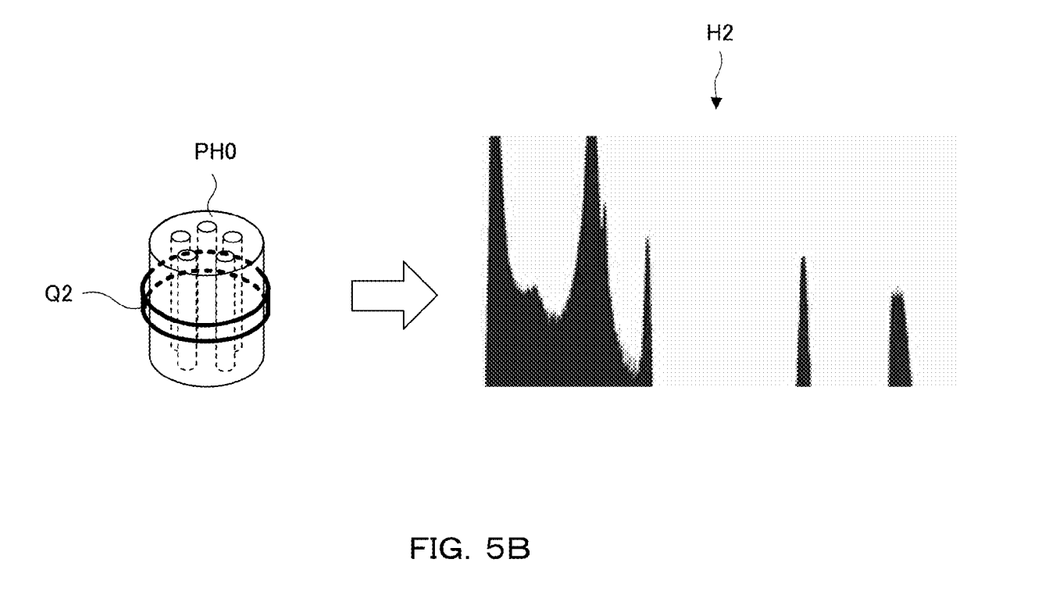
FIG. 5B is a drawing showing an image region for which a histogram is to be obtained and an example of the histogram.

Meanwhile, CT image data for which a histogram is to be produced may be limited to those of a part of region of the phantom PH0, instead of those of the whole of the phantom PH0. FIGS. 5A and 5B are drawings showing examples of image regions for which respective histograms are to be obtained and the histograms thereof. It is known that, generally in an X-ray CT apparatus using a two-dimensional detector and a cone beam emitting X-ray tube, reliability of image values lying in positions away from the central region in the slice direction of an image is low (a fault of Feldkamp reconstruction algorism). Accordingly, as compared with a histogram H1 that uses a whole image region Q1 as shown in FIG. 5A, a histogram H2 that uses an image region Q2 limited along a direction with a uniform density from the central cross-section (for example, a region having a constant thickness within around 20% of a scan range from the center of the scan range in the slice direction) as shown in FIG. 5B has a higher probability that peaks are clearly separated. Therefore, when intended separability of peaks cannot be obtained using the whole image region, separability of peaks can be improved by limiting an image region to be used.

FIG. 6 is a drawing showing a histogram and ranges R0 to R4 of a prescribed number of counts. Upon detecting a peak, for example, peaks P0 to P4 that fall within the ranges R0 to R4 of the number of counts can be detected from a higher CT value. In the example in FIG. 6, the part HA4 in the phantom PH0 corresponds to the peak P4 specified by the range R4 of number of counts, the part HA3 corresponds to the peak P3 specified by the range R3 of number of counts, the part HA2 corresponds to the peak P2 specified by the range R2 of number of counts, the part HA1 corresponds to the peak P1 specified by the range R1 of number of counts, and the part HA0 corresponds to the range R0 of number of counts.

(Determination of Calibration Curve)

Further, for peaks P0 to P4 specified by respective ranges R0 to R4, CT values representing respective peaks can be specified. The representative value may be, for example, a CT value at which a peak takes the maximum value, or an average value of CT values at a peak. Further, it may be a CT value at which a fitted function takes the maximum value.

Figure 7:
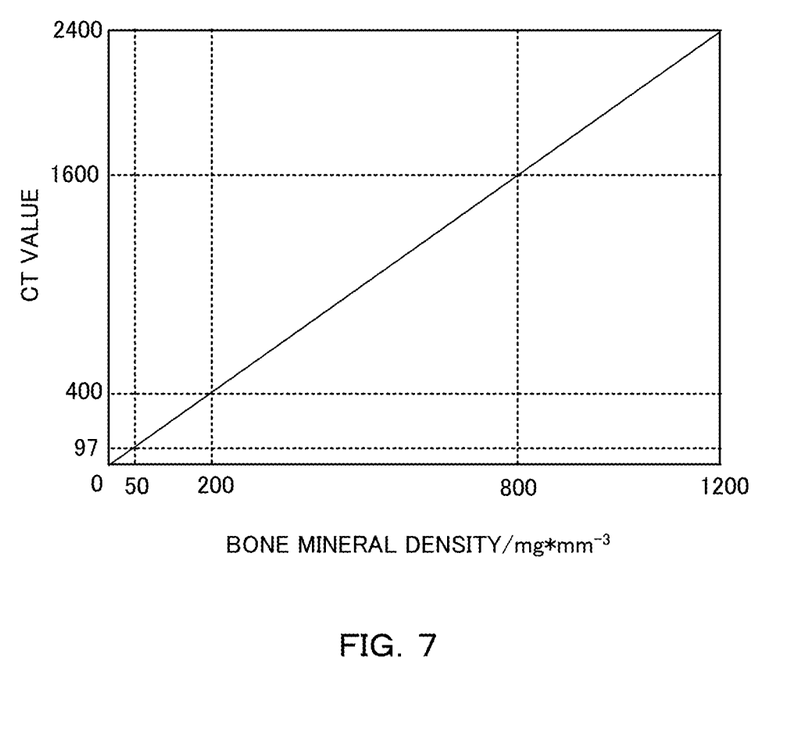
FIG. 7 is a drawing showing a determined calibration curve.

FIG. 7 is a drawing showing a determined calibration curve. The calibration curve can be calculated by plotting known bone mineral densities corresponding to respective peaks P0 to P4 relative to CT values representing the detected respective peaks P0 to P4, and drawing a straight line based on the least-square approach etc. Further, the once calculated calibration curve is stored as the correspondence between the CT value and bone mineral density, and it is possible to easily convert CT image data of a subject into a bone mineral density by using the curve.

(Output of Analysis Result)

Figure 8:
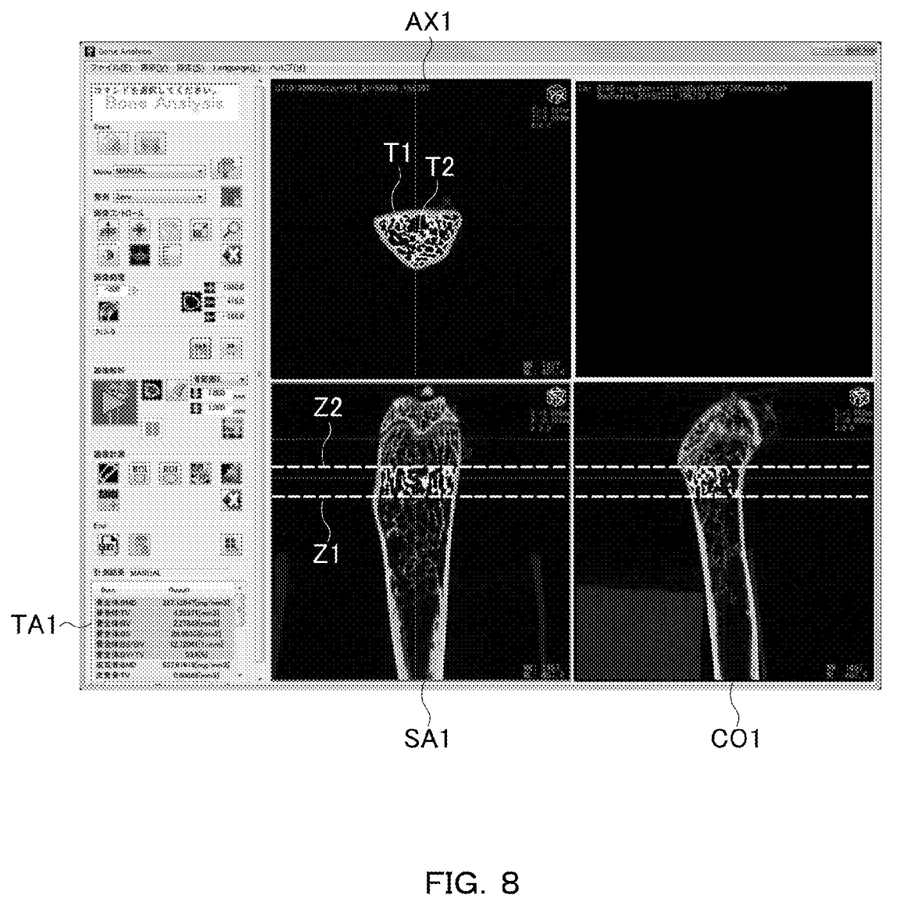
FIG. 8 is a drawing showing a screen that displays an analysis result of bone mineral density of a subject.

It is possible to calculate bone mineral density data from the CT image data of a subject by using the correspondence between the CT value and bone mineral density determined as a calibration curve. Then, the analysis result obtained in this way can be displayed on a display screen. FIG. 8 is a drawing showing a screen displaying a bone mineral density analysis result of a subject. Respective displays of cross-section images in FIG. 8 are displays on an axial plane AX1, a sagittal plane SA1, and a coronal plane CO1.

The axial plane is a plane vertical to the body axis direction of a subject. The sagittal plane is a plane vertical to the body width direction of a subject. The coronal plane is a plane vertical to the body thickness direction of a subject. A part corresponding to a cortical bone T1 and a part corresponding to a trabecular bone T2 are displayed based on the difference in color density. In the sagittal plane SA1 and the coronal plane CO1 in particular, a part corresponding to the cortical bone T1 and a part corresponding to the trabecular bone T2 in a prescribed range Z1-Z2 in the longitudinal direction of the bone are displayed.

In the screen display example shown in FIG. 8, respective characteristic values are also shown as a table TA1 showing a bone mineral density analysis result. For the prescribed range Z1-Z2 in the longitudinal direction of the bone, characteristic values of the whole bone, the cortical bone and the trabecular bone can be calculated.

Figure 9:
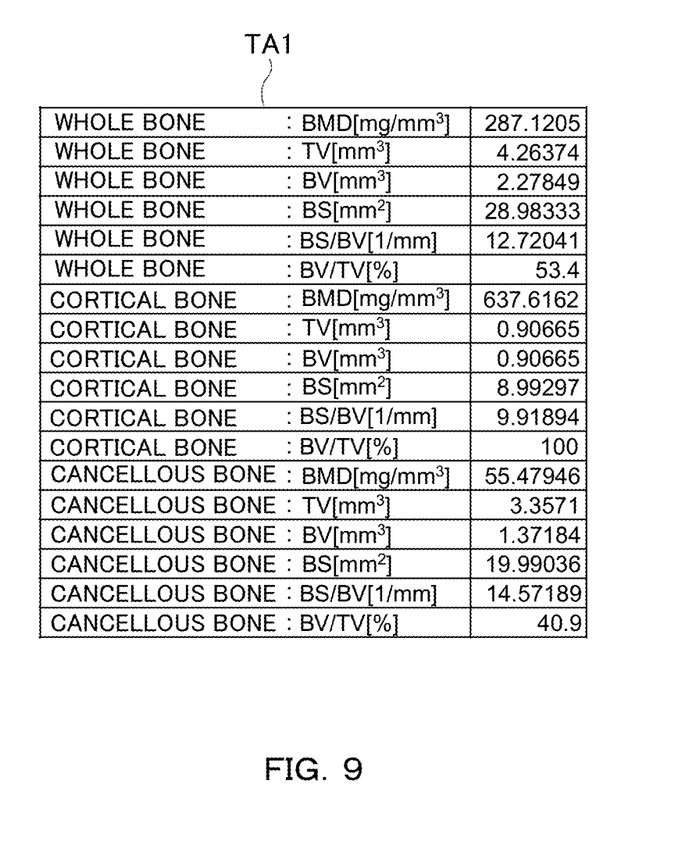
FIG. 9 is a table showing an analysis result of bone mineral density of a subject.

FIG. 9 shows the table TA1 showing a bone mineral density analysis result of a subject. In the example shown in FIG. 9, the bone mineral density of the whole bone is 287 mg/mm$^3$, the bone mineral density of the cortical bone is 638 mg/mm$^3$, and the bone mineral density of the trabecular bone is 55 mg/mm$^3$.

DESCRIPTION OF REFERENCE SIGNS 10 measurement system
50 X-ray CT apparatus
100 analyzer
101 CT image data storage part
102 histogram production part
105 known data storage part
106 correspondence determination part
107 correspondence storage part
108 region display part
109 analysis part
HA0 to HA4 specific bone mineral density part
P0 to P4 peak
PH0 phantom
Q1, Q2 image region
R0 to R4 range of the number of count
SA1 sagittal plane
CO1 coronal plane
AX1 axial plane
T1 cortical bone
T2 trabecular bone
Z1-Z2 range

What is claimed is:

1. An analyzer of bone mineral density using CT image data, created from a CT scanner, of a phantom having a known bone mineral density, the analyzer comprising:
a known data storage part that stores known data of bone mineral density for a phantom;
a processor configured to perform on or more of:
a histogram production that produces a histogram of region number relative to a CT value for three-dimensional CT image data of the phantom;
a correspondence determination that receives said histogram from said histogram production and determines correspondence between a CT value and a bone mineral density by correlating CT values showing respective peaks of the produced histogram with the known data of the phantom; and
an analysis that receives the correspondence between the CT value and bone density determined by the correspondence determination and decides a bone mineral density for three-dimensional CT image data of a subject using the determined correspondence and outputs said determined bone mineral density,
wherein the correspondence determination discriminates that, when a peak is included in a range of a prescribed number of counts of the produced histogram, the peak is one to be correlated with the known data.

2. The analyzer according to claim 1, further comprising a display that displays on a screen a region of three-dimensional CT image data of the phantom showing a peak to be correlated with the known data.

3. The analyzer according to claim 1, wherein the correspondence determination determines a calibration curve between a CT value and a bone mineral density as the determined correspondence.

4. The analyzer according to claim 1, wherein the histogram production produces a histogram of region number relative to a CT value using data of regions limited along a direction in which density of the phantom is uniform, in the three-dimensional CT image data.

5. An analysis method of bone mineral density using CT image data, created from a CT scanner, of a phantom having a known bone mineral density, comprising the steps of:

producing a histogram of region number relative to a CT value for three-dimensional CT image data of the phantom;

determining correspondence between a CT value and a bone mineral density by correlating CT values showing respective peaks of the produced histogram with known data of bone mineral density stored with respect to the phantom; and deciding a bone mineral density for three-dimensional CT image data of a subject using the determined correspondence and outputs said decided bone mineral density, wherein the correspondence determination discriminates that, when a peak is included in a range of a prescribed number of counts of the produced histogram, the peak is one to be correlated with the known data.

6. A recording medium, which is a computer readable and non-transitory recording medium, recording an analysis program of bone mineral density that is to be executed by a computer using CT image data, created from a CT scanner, of a phantom having a known bone mineral density, the analysis program comprising the processes of:

producing a histogram of region number relative to a CT value for three-dimensional CT image data of the phantom;

determining correspondence between a CT value and a bone mineral density by correlating CT values showing respective peaks of the produced histogram with known data of bone mineral density stored with respect to the phantom; and deciding a bone mineral density for three-dimensional CT image data of a subject using the determined correspondence and outputs said decided bone mineral density, wherein the correspondence determination discriminates that, when a peak is included in a range of a prescribed number of counts of the produced histogram, the peak is one to be correlated with the known data.

* * * * *